United States Patent
Miyata et al.

(10) Patent No.: US 7,182,757 B2
(45) Date of Patent: Feb. 27, 2007

(54) MEDICAL GUIDE WIRE

(75) Inventors: Naohiko Miyata, Aichi-ken (JP); Tomihisa Kato, Aichi-ken (JP); Hiroshi Minamihata, Aichi-ken (JP); Yoshiyuki Arasawa, Aichi-ken (JP)

(73) Assignee: Asahi Intecc Co., Ltd., Nagoya (JP)

( * ) Notice: Subject to any disclaimer, the term of this patent is extended or adjusted under 35 U.S.C. 154(b) by 0 days.

(21) Appl. No.: 11/018,394

(22) Filed: Dec. 22, 2004

(65) Prior Publication Data
US 2005/0154371 A1  Jul. 14, 2005

(30) Foreign Application Priority Data
Dec. 25, 2003   (JP) .............................. 2003-428575

(51) Int. Cl.
*A61M 5/178* (2006.01)
*A61M 25/00* (2006.01)
(52) U.S. Cl. ................. 604/528; 604/164.13; 604/272; 604/510; 600/585
(58) Field of Classification Search ................. 604/170, 604/164, 165, 169, 585, 510, 528, 164.13, 604/103.09, 525–527; 600/585
See application file for complete search history.

(56) References Cited

U.S. PATENT DOCUMENTS

| | | | |
|---|---|---|---|
| 4,650,472 A | 3/1987 | Bates | |
| 4,850,960 A * | 7/1989 | Grayzel | 604/510 |
| 4,951,686 A | 8/1990 | Herlitze | |
| 5,103,543 A | 4/1992 | Hodgson | |
| 5,373,856 A | 12/1994 | Grenouillet | |
| 5,478,328 A * | 12/1995 | Silverman et al. | 604/272 |
| 5,527,298 A * | 6/1996 | Vance et al. | 604/528 |
| 6,171,326 B1 * | 1/2001 | Ferrera et al. | 606/191 |
| 6,610,046 B1 * | 8/2003 | Usami et al. | 604/530 |
| 6,881,194 B2 * | 4/2005 | Miyata et al. | 600/585 |
| 2005/0027212 A1 * | 2/2005 | Segner et al. | 600/585 |

FOREIGN PATENT DOCUMENTS

| | | |
|---|---|---|
| JP | 10-118192 | 5/1998 |
| WO | WO 00/57944 | 10/2000 |
| WO | WO 02/47755 A2 | 6/2002 |
| WO | 1 243 283 A2 | 9/2002 |
| WO | WO 2005/016433 A2 | 2/2005 |

* cited by examiner

*Primary Examiner*—Kevin C. Sirmons
*Assistant Examiner*—Andrew Gilbert
(74) *Attorney, Agent, or Firm*—Morgan, Lewis & Bockius, LLP (57) ABSTRACT

In a medical guide wire (1) formed by a helical hollow wire body which is arranged to retractably move against a needle tip (6), the helical hollow wire body is formed into a wire-stranded helical hollow tube (2) by stranding a multitude of wire coil elements (3). The wire coil elements (3) of a wire-stranded helical hollow tube (2) has a stranding angle ($\theta 1$) of 55 degrees or less against an axial direction of the wire-stranded helical hollow tube (2), and having an angle more than plus 2 degrees or an angle less than minus 2 degrees against a knife edge angle ($\theta 2$) of the needle tip (6), thus preventing the wire coil elements (3) from inadvertently hitched in the needle tip (6), and thereby enabling manipulators to a smooth insertion and pull operation so as to improve a curability when the wire-stranded helical hollow tube (2) is retractably manipulated against the needle tip (6).

5 Claims, 5 Drawing Sheets

MEDICAL GUIDE WIRE

BACKGROUND OF THE INVENTION

1. Field of the Invention

The invention relates to a medical guide wire which is therapeutically arranged to retractably move against a tip of a puncture needle set in advance into an arteria carotis interna in a remedial method (venipuncture) to insert a central venous catheter into the arteria carotis interna.

2. Description of Related Art

Upon implementing the venipuncture to insert a central venous catheter into the arteria carotis interna, an insertion tool for a medical guide wire has been used to unerringly insure the insertion safely against the arteria carotis interna with a simple procedure as represented by Japanese Laid-open Patent Application No. 10-118192 (referred to simply as "first reference" hereinafter).

The insertion tool for the medical guide wire has a puncture needle and a side support member which are to be removably attached to a syringe cylinder. The puncture needle is manipulated beforehand to puncture the needle tip into an appropriate point of the venous vessel, and then, the medical guide wire is inserted into the venous vessel through the side support member.

In the meanwhile, the medical guide wire (abbreviated as "the guide wire" hereinafter) is inserted into a tortuous and thin vascular vessel to introduce a distal end of the guide wire into a diseased lesion by manipulating (push-pull and turn) a band access portion placed outside a subject patient.

In order to achieve a smooth manipulation when inserting the guide wire into the vascular vessel, it is required for the guide wire to have certain multi-mechanical properties. The multi-mechanical properties include a high flexibility, a good straightness in an unrestricted free state and a good restitutivity from the deformed configuration. The guide wire of this type is required at its distal end portion to have a high flexibility, while at the sane time, required at its rear portion to have an appropriate rigidity as a functionally gradient property. It is also indispensable for the distal end to have a high maneuverability in which the distal end properly responds to the manipulation which is to be done at the hand access portion outside the subject patient.

The guide wire is generally formed by winding a single one wire (not stranded wires but an ordinary single line wire) into a hollow tube structure in which an elongated core is inserted. Both end portions of the hollow tube structure are fixed to the elongated core by means of soldering procedure.

Figure 14:
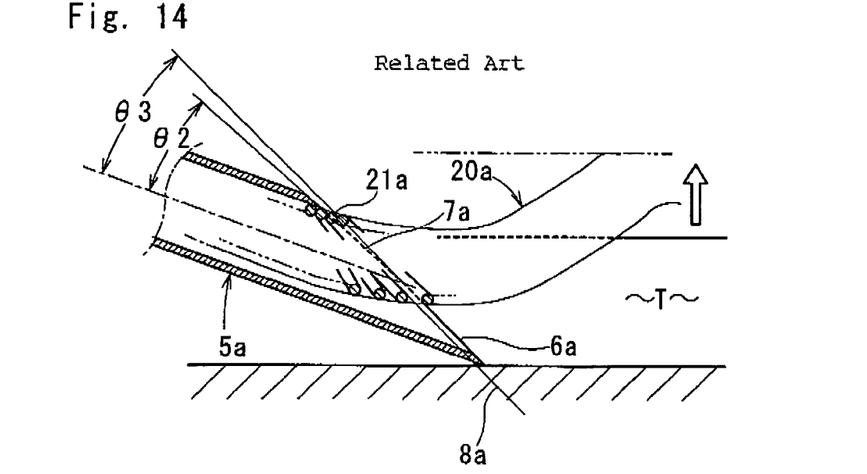
FIG. 14 is a longitudinal cross sectional view of a related art medical guide wire.

Upon inserting the central venous catheter into the arteria carolis interna, the puncture needle 5a is set into the arteria carotis interna near a common carotid artery as shown in FIG. 14. The needle tip 6a has a rake surface end sharpened by cutting the puncture needle 5a with two-stop angles ($\theta 2$, $\theta 3$) against its axial direction (e.g., $\theta 2$=18–22 degrees). In order to precisely puncture the arteria carotis interna which is diametrically smaller than a maximum breadth of the rake surface end of the needle tip 6a, it is necessary for the manipulator to suppress the blood vessel T with his or her fingers to inflate it as shown at the phantom line in FIG. 14 until the manipulator feels the blood regurgitation to confirm that the punctured position is appropriate.

Figure 15:
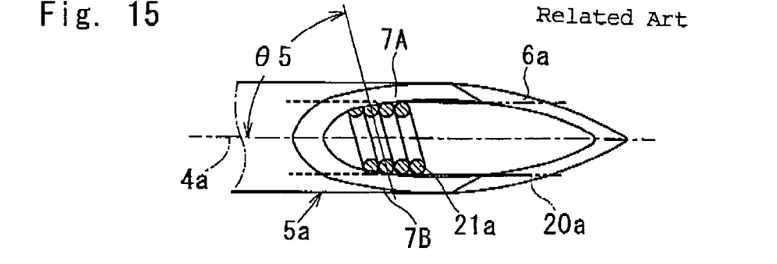
FIG. 15 is a plan view of a needle tip of the related art puncture needle.
Figure 16:
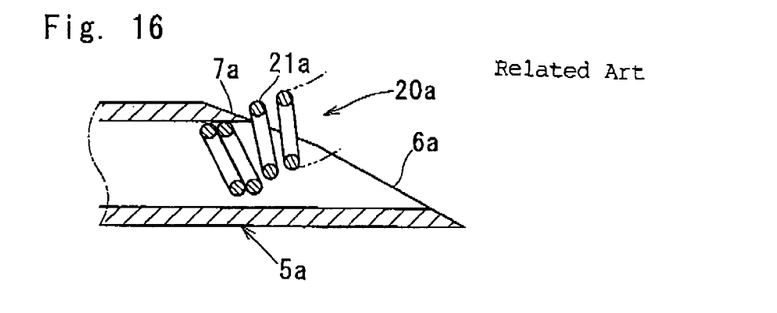
FIG. 16 is a longitudinal cross sectional view of the related art medical guide wire partly shown.

Thereafter, as shown FIGS. 14, 15 and 16, the guide wire 20a is inserted into the puncture needle 5a through the side support member (not shown). Then, the puncture needle 5a is pulled from the blood vessel T to inserted the central venous catheter (not shown) into the guide wire 20a. This manipulation requires highly skilled techniques so that the manipulator would often have to repeat the pull and puncture procedure several times until he or she gets accustomed to appropriately puncture in the venipuncture procedure.

Figure 17:
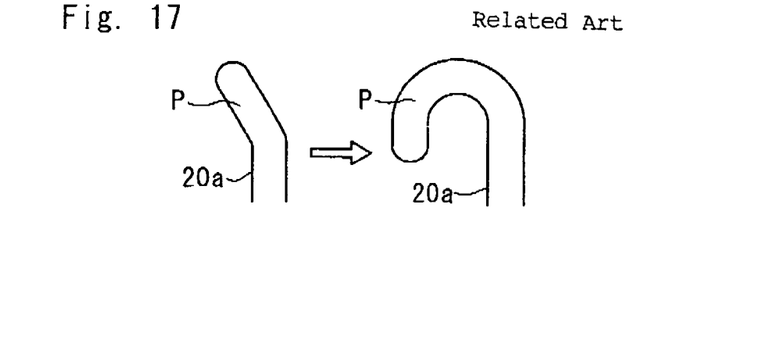
FIG. 17 is an explanatory view of a preshaped tip in the related art medical guide wire.

Meanwhile, the distal end of the guide wire 20a has a preshaped portion (P) plastically deformed into a U-shaped or dog-legged configuration by a finger tip operation in order to smoothly insert the guide wire 20a into the blood vessel T. For this reason, upon inserting the guide wire 20a through the needle tip 6a, the preshaped portion (P) causes the guide wire 20a to bend upward with the needle tip 6a and the vascular wall as fulcra.

Since the guide wire 20a is formed by winding the single one wire into helical coil structure, the pull operation against the guide wire 20a likely causes to induce a helical clearance between the wire coil elements 21a of the helical coil structure. When the guide wire 20a is manipulatively bent, the bending force against the guide wire 20a also likely causes to induce clearance between the wire coil elements 21a of the helical coil structure, as is often the case with a general helical spring which is likely to apear the clearance between the wire coil elements when pulled in the lengthwise direction 4a. This often makes the needle tip 6a hitch its edge portion 7a in the wire coil elements 21a upon insertably slide the guide wire 20a into the puncture needle 5a.

In the situation in which the guide wire 20a is deformed upward into a bow-shaped configuration within the puncture needle 5a so as to appear a minute clearance between the wire coil elements 21a, the pulling operation against the guide wire 20a increases the minute clearance to make the wire coil elements 21a likely hitch in knife edge ends 7A, 7B of the edge portion 7a due to the sliding resistance against the puncture needle 5a as shown in FIGS. 15 and 16. The hitching incident against the knife edge ends 7A, 7B occasions the guide wire 20a to retract inside the rake surface end of the edge portion 7a to likely engage it with an inner surface of the puncture needle 5a.

In this instance, the wire coil elements 21a of the guide wire 20a generally forms an angle ($\theta 5$) in the range of 78 to 82 degrees against an axial direction 4a of the puncture needle 5a.

When forcibly pulling the guide wire 20a from the puncture needle 5a with the edge portion 7a hitched in the wire coil elements 12a, the pulling force likely causes the guide wire 20a to rupture its thin single wire coil structure. The pulling force also induces a reactional twitch against the puncture needle 5a to make it mistakenly pierce into the common carotid artery near the blood vessel (arteria carotis interna) T so as to invite complications all the more difficult to cure.

Therefore, it is an object of the invention to overcome the above drawbacks, and provide a medical guide wire which is capable of eliminating a possibility to hitch a puncture needle in wire coil elements of the guide wire so as to smoothly insert into and pull from the puncture needle to resultantly improve the curability significantly against the diseased area.

SUMMARY OF THE INVENTION

According to the present invention, there is provided a guide wire which is formed by a helical hollow wire body arranged to retractably move against a needle tip of a puncture needle. The helical hollow wire body is formed into a wire-stranded helical hollow tube by stranding a multitude of wire coil elements. The wire coil elements of the wire-stranded helical hollow tube have a stranding angle of 55 degrees or less against an axial direction of the wire-stranded helical hollow tube, and further having an angle more than plus 2 degrees upward or an angle less than minus 2 degrees downward against a knife edge angle of said needle tip as an angular range.

The wire-stranded helical hollow tube is such that the bending force makes the wire coil elements relatively slide, thus making the wire coil elements engaged each other to prevent then from appearing a clearance between the wire coil elements, as opposed to the single wound wire coil which is likely to appear the clearance between the wire coil elements easily as the total bending angle increases more. This effectively prevents an edge portion of the puncture needle from invading into the wire coil elements, and thereby making it possible to smoothly insert the guide wire into and pull from the puncture needle. A certain number of the wire coil elements are formed from a single one wire or stranded wires, and stranded into a rope-shaped configuration to form them into the wire-stranded helical hollow tube which rarely appears the clearance between the wire coil elements when manipulatively bended.

Based on the statistic data derived from the experimentations repeatedly done many times by using various types of specimens, the stranding angle is determined as for the wire coil elements of the wire-stranded helical hollow tube. The stranding angle enables the manipulator to feel a reduced resistance accompanied when pulling the guide wire from the needle tip so as to insure a smooth and quick pulling operation for the guide wire.

According to other aspect of the present invention, the wire coil elements of the helical hollow wire body is formed from stranded wires. The wire coil elements of the helical hollow wire body have a stranding direction mutually opposite to a stranding direction which the wire coil elements of the wire-stranded helical hollow tube has. The stranding wires of the wire coil elements have a stranding direction substantially in parallel with an axial direction of the helical hollow wire body.

This enhances the sliding performance of the guide wire against the puncture needle so as insure a smooth insertablity and pulling operation against the puncture needle.

In order to reinforce the above advantages, the following structures are adopted.

According to other aspect of the present invention, the wire coil elements of the helical hollow wire body are formed from stranded wires.

According to other aspect of the present invention, the stranded wires of the wire-stranded helical hollow tube has an outer surface diametrically reduced.

According to other aspect of the present invention, the puncture needle is combined in pairs.

According to other aspect of the present invention, a head plug is provided to both ends of a main wire line which forms the wire-stranded helical hollow tube.

According to other aspect of the present invention, a U-shaped or dog-legged tip is preshaped as a preshaped tip at a distal end of the wire-stranded helical hollow tube.

BRIEF DESCRIPTION OF THE DRAWINGS

Preferred forms of the present invention are illustrated in the accompanying drawings in which.

DETAILED DESCRIPTION OF THE PREFERRED EMBODIMENTS

In the following description of the depicted embodiments, the same reference numerals are used for features of the same type.

Referring to FIGS. 1 through 10 which show a medical guide wire 1 according to a first embodiment of the invention, the medical guide wire 1 (abbreviated as "guide wire 1" hereinafter) is formed by a helical hollow wire body which is arranged to retractably move against a needle tip 6 of a puncture needle 5. The helical hollow wire body is formed into a wire-stranded helical hollow tube 2 by stranding a multitude of wire coil elements 3. The wire coil elements 3 may be of stranded wires or a single one wire.

Figure 1:
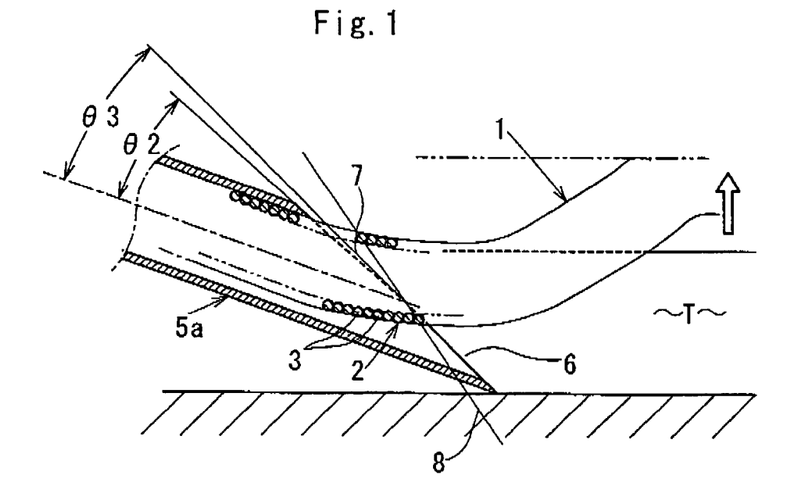
FIG. 1 is a longitudinal cross sectional view of a medical guide wire according to a first embodiment of the invention.
Figure 3:
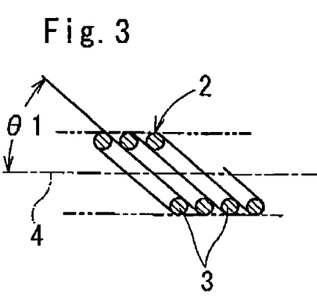
FIG. 3 is a longitudinal cross sectional view of a medical guide wire only partly shown.

The wire coil elements 3 of the wire-stranded helical hollow tube 2 have a stranding angle ($\theta 1$) of 55 degrees or less against an axial direction 4 of the wire-stranded helical hollow tube 2. The wire coil elements 3 further have an angle of more than plus 2 degrees upward or an angle of less than minus 2 degrees downward against a knife edge angle ($\theta 2$) of the needle tip 6 as an angular range.

Figure 2:
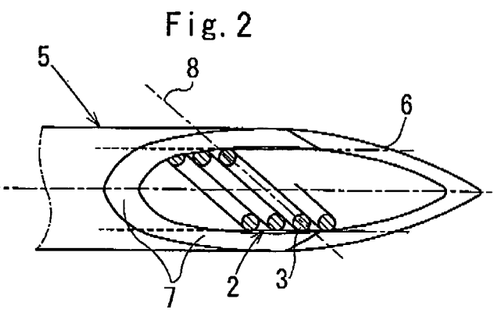
FIG. 2 is a plan view of a needle tip of a puncture needle.
Figure 4:
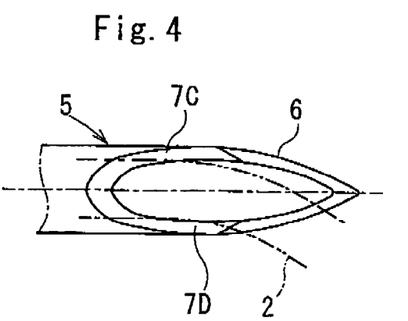
FIG. 4 is a plan view of the needle tip of the puncture needle.

As for an intersectional direction between extension lines each along the stranding angle ($\theta 1$) and the knife edge angle ($\theta 2$), the intersectional direction is oppositely different between at a front elevational side and a rear elevational side of the needle tip 6. It is sufficient to only determine the stranding angle ($\theta 1$) and the angular differential requirement merely at either the front elevational side or the rear elevational side of the needle tip 6.

As to the knife edge angle ($\theta 2$), among the two-step rake angles ($\theta 2$) and ($\theta 3$) which are provided with the needle tip 6, the knife edge angle ($\theta 2$) is to have a close-sliding relationship with the guide wire 1.

With the guide wire 1 thus structured, the wire-stranded helical hollow tube 2 is such that the bending force makes the wire coil elements 3 relatively slide, thus making the wire coil elements 3 engaged each other to prevent them from appearing a clearance between the wire coil elements 3. This effectively prevents an edge portion 7 of the puncture needle 5 from invading into the wire coil elements 3, and thereby making it possible to smoothly insert the guide wire 1 into and pull from the puncture needle 5. A certain number of the wire coil elements 3 are formed from the single one wire or the stranded wire, and stranded into a rope-shaped configuration to form them into the wire-stranded helical hollow tube 2 which rarely appears the harmful clearance between the wire coil elements 3 even when manipulatively bended.

Based on the statistic data derived from the experimentations repeatedly carried out by using various types of specimens, the stranding angle is determined as for the wire coil elements 3 of the wire-stranded helical hollow tube 2. The stranding angle enables the manipulator to feel a reduced resistance accompanied when pulling the guide wire from the needle tip so as to insure a smooth and quick pulling operation for the guide wire 1.

Figure 6:
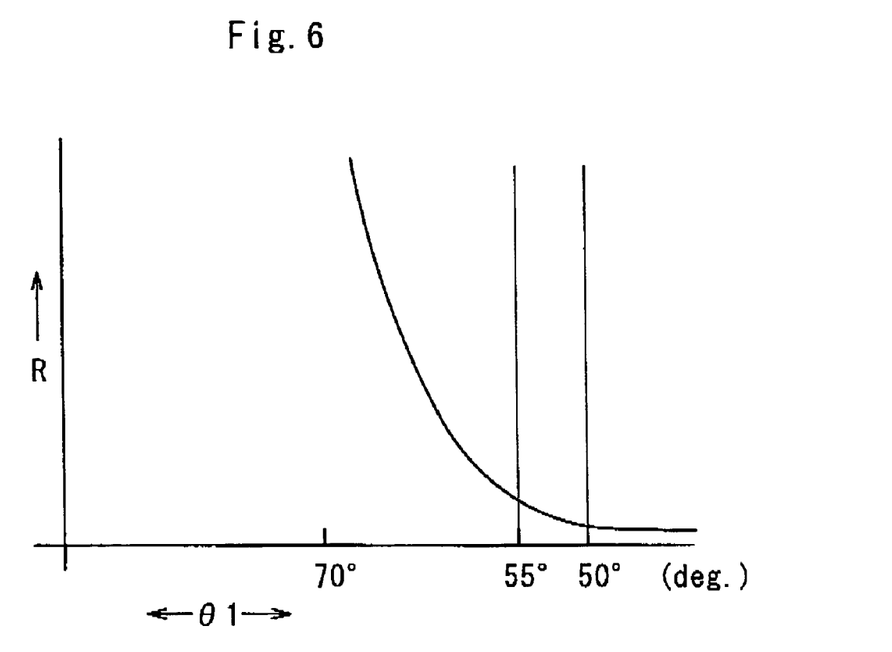
FIGS. 6 and 7 are graphical representations characteristic of the medical guide wire.

As for the characteristics represented by pulling out the guide wire 1 from the puncture needle 6, FIG. 6 shows that the resistance against the pulling operation significantly reduces when the stranding angle ($\theta 1$) reaches 55 degrees and beyond. In this instance, the stranding angle ($\theta 1$) is equivalent to helical lead angle formed against a central line 4 of the wire-stranded helical hollow tube 2 as shown in FIG. 3.

As opposed to the related art depicted in FIGS. 14 through 17, the characteristics based on the stranding angle ($\theta 1$) being less than 55 degrees means to prevent the edge portion 7 (knife edge ends 7C, 7D) from inadvertently hitching in the wire coil elements 3 of the wire-stranded helical hollow tube 2.

As to the angle of more than plus 2 degrees or an angle of less than minus 2 degrees against a knife edge angle ($\theta 2$) of the needle tip 6, these angular determinations makes the stranding angle ($\theta 1$) smaller than a winding angle which appears when the helical, coil structure is formed by winding a single one wire when the stranding angle ($\theta 1$) becomes equal to the knife edge angle ($\theta 2$) of the needle tip 6, the angle ($\theta 1$) would accidentally cause the wire coil elements 3 to lightly hitch either one of the knife edge ends 7C, 7D of the needle tip 6.

Figure 11:
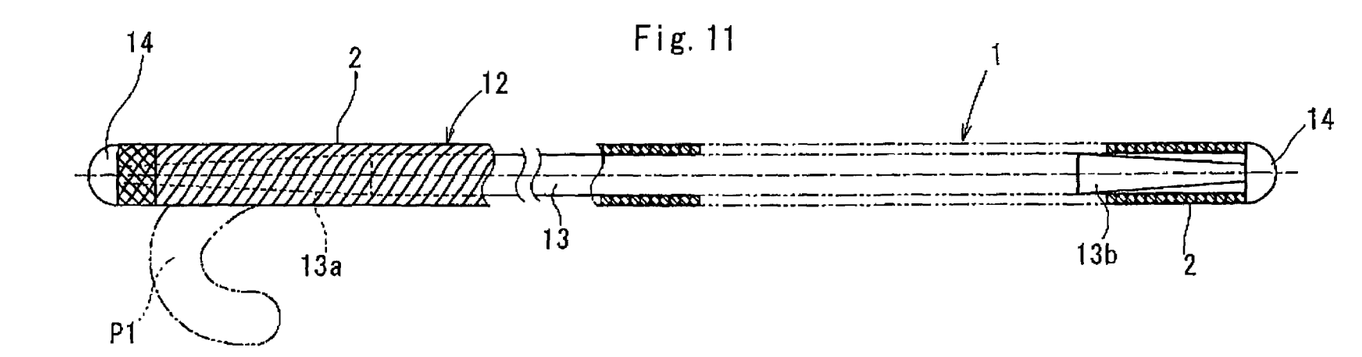
FIG. 11 is a side elevational view of a medical guide wire partly sectioned according to a second embodiment of the invention.

The angular differential requirement ($\theta 1-\theta 2$) effectively prevents the knife edge ends 7C, 7D from invading into the wire coil elements 3. This is particularly advantageous when a distal end of the guide wire 1 is formed into a U-shaped or dog-legged configuration (P1) as shown in FIG. 11 as other embodiment of the invention.

Figure 7:
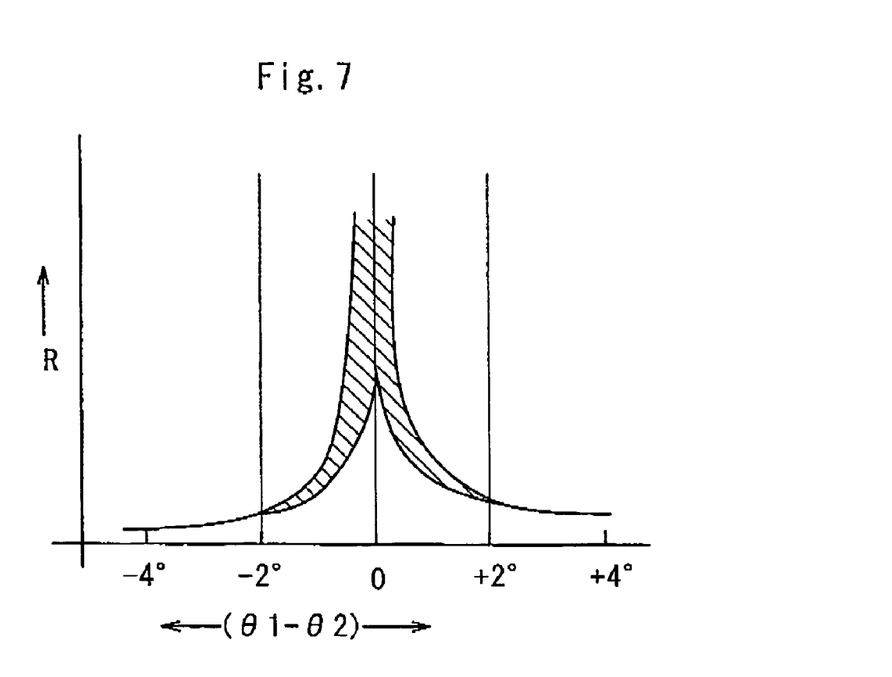
Figure 8:
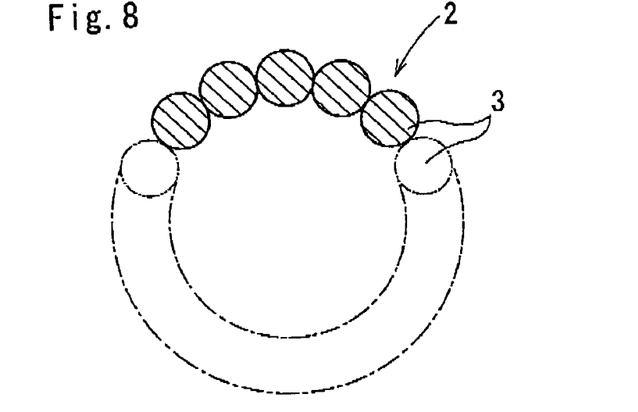
FIGS. 8, 9 and 10 are latitudinal cross sectional views of the wire-stranded helical hollow tube.
Figure 9:
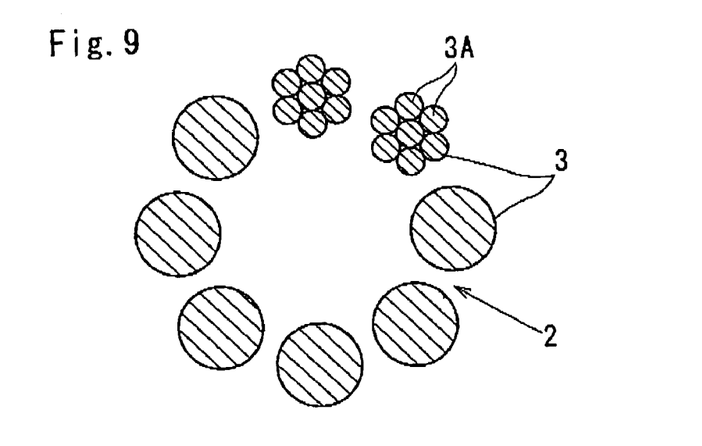
Figure 10:
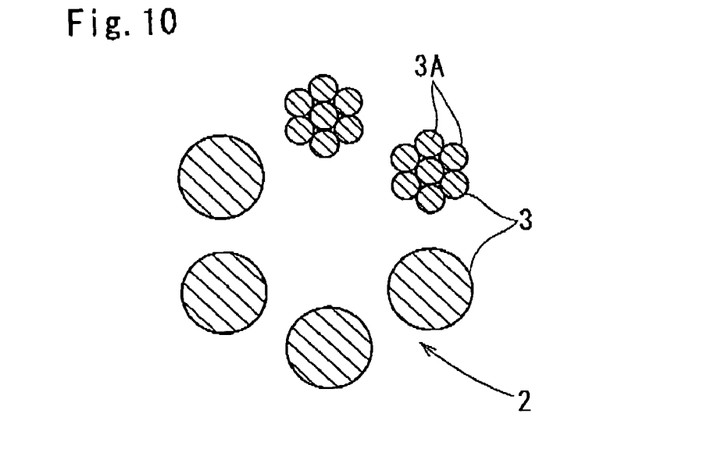

FIG. 7 shows a relationship between the angular differential requirement ($\theta 1-\theta 2$) and the pulling resistance R. It is found from FIG. 7 that the pulling resistance R significantly fall when the angular differential requirement ($\theta 1-\theta 2$) is more than plus 2 degrees and less than minus 2 degrees. When the stranding angle ($\theta 1$) becomes equal or near to the knife edge angle ($\theta 2$), the pulling resistance R is apparently found to increase rapidly.

By determining the stranding angle ($\theta 1$) to be less than 55 degrees, the smaller stranding angle ($\theta 1$) makes the wire coil elements 3 incline snore. This prevents the wire coil elements 3 from being retained at both the knife edge ends 7C, 7D concurrently so as to engage the wire coil elements 3 with either one of the knife edge ends 7C, 7D.

Figure 5:
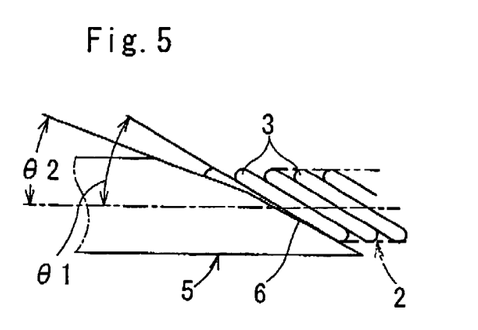
FIG. 5 is a side elevational view of the needle tip and a wire-stranded helical hollow tube depicted how they works.

By additionally setting the angular differential requirement ($\theta 1-\theta 2$) to be more than plus 2 degrees, a relative angular difference is obtained between the knife edge angle ($\theta 2$) of the needle tip 6 and a slantwise direction 8 defined when connecting the neighboring wire coil elements 3 upon engaging the guide wire 1 with the edge portion 7 when turning the guide wire upward at an entrance of the arteria carotia interna T. This reveals an intersectional configuration between an extension along the knife edge angle ($\theta 2$) and the slantwise direction 8 along a space appeared between the neighboring wire coil elements 3.

With the angular differential requirement ($\theta 1-\theta 2$) set to be less than minus 2 degrees, it is possible to insure the intersectional configuration, the relative angular difference and the engaging condition of the wire coil elements 7 brought against the edge portion 7 in the same manner mentioned above. This effectively prevents the knife edge ends 7C, 7D from invading into the wire coil elements 3 so as smoothly insert the guide wire 1 into and pull from the puncture needle 5 with a good sliding performance.

With the angular differential requirement ($\theta 1-\theta 2$) set to be more than plus 2 degrees, the case makes it possible to increase the stranding angle ($\theta 1$) greater compared to the counterpart case in which the angular differential requirement ($\theta 1-\theta 2$) is set to be less than minus 2 degrees. This is convenient especially upon forming the wire-stranded helical hollow tube 2 diametrically larger and more flexibly.

With the angular differential requirement ($\theta 1-\theta 2$) set to be less than minus 2 degrees, the case makes it possible to decrease the stranding angle ($\theta 1$) smaller. This is convenient especially upon forming the wire-stranded helical hollow tube 2 by the thin wire coil elements 3 with a high rigidity.

This makes it possible to readily insert the guide wire 1 into the puncture needle 5 with a good maneuverability, and making the diametrically reduced guide wire 1 less intrusive for the subject patient so as to mitigate the burden the subject patient suffers.

With the guide wire 1 thus described, the stranding angle ($\theta 1$) and the angular differential requirement ($\theta 1-\theta 2$) are such that the manipulatability is significantly improved upon inserting the guide wire 1 into and pulling it from the arteria carotis interna T through the puncture needle 5. This renders the manipulative procedures efficient and smooth when operating the puncture needle 5 to pierce into arteria carotis interna T in the therapeutical method to insert the central venous catheter in to the arteria carotis interna, thus significantly enhancing the curability so as to relieve the pains of the subject patient.

As shown in Table 1, dimensional designs are raised as product specimens A, B and C of the guide wire 1 in which the wire coil elements 3 has the stranding angle ($\theta 1$), and the needle tip 6 has the knife edge angle ($\theta 2$) as specified hereinbefore.

TABLE 1

| | $\theta 1$ | $\theta 2$ | Wire-stranded helical hollow tube 2 |
|---|---|---|---|
| specimen A | 18 deg. | 22 deg. | 18 single wire coil elements 3 stranded to be 0.42 mm in diameter with line diameter as 0.058 mm (see FIG. 8) |
| specimen B | 40.5 deg. | 19 deg. | 7 single wires 3A stranded to form the wire coil elements 3 (1 × 7 structure). 8 wire coil elements 3 stranded to be 0.86 mm in diameter with line diameter as 0.06 mm (see FIG. 9) |
| specimen C | 32 deg. | 19 deg. | 7 single wires 3A stranded to form the wire coil elements 3 (1 × 7 structure). 6 wire coil elements 3 stranded to be 0.49 mm in diameter with line diameter as 0.04 mm (see FIG. 10) |

Among the three specimens A, B and C, the latter two specimens B and C have the stranded wires at the wire coil elements 3 so as to make the guide wire 1 more flexible based on the pliable property peculiar to the stranded wires.

With the wire-stranded helical hollow tube 2 formed from wire coil elements 3, as shown in Table 2, it is possible to reinforce the tensile rupture strength for the wire-stranded helical hollow tube 2 so as to prevent the guide wire 1 from inadvertently broken while manipulating it to give the subject patient the therapeutical procedures. It is convenient for the users when the guide wire 1 is produced with the puncture needle 5 combined in pairs.

TABLE 2

| | single wound wires (related art) | stranded wires (subject invention) |
|---|---|---|
| 0.45 mm in diameter | 15.7N (tensile rupture strength) (line diameter: 0.1 mm) | 50N diameter of stranded wires (1 × 7): 0.10 mm (8 wires stranded) |
| 0.79 mm in diameter | 60N (line diameter: 0.2 mm) | 146.5N diameter of stranded wires (1 × 7): 0.20 mm (8 wires stranded) |

Upon forming the wire-stranded helical hollow tube 2 to produce the specimens A, B and C, the wire coil elements 3 are wound around a core member (not shown) with the use of a twisting machine (not shown) to provide a wound wire structure. Then, the core member is withdrawn after the wound wire structure is heat treated. Alternatively, the wire coil elements 3 are stranded along a predetermined circle line to form them into a helical coil structure. What instrument is used to provide the stranding angle ($\theta 1$) will be decided depending on the stranded number and diametrical dimension of the wire coil elements 3 to produce. The stranding angle ($\theta 1$) can be adjusted in some degrees depending on the twisting force applied to the wire coil elements 3.

FIG. 11 shows a second embodiment of the invention in which a head plug 14 is provided to give the guide wire 1 a smooth entry into the vascular vessel. The guide wire 1 has a main wire portion 12 at the wire-stranded helical hollow tube 2 into which an elongation core 13 is inserted. To both open ends of the main wire portion 12, the head plug 14 is secured.

In this instance, the main wire portion 12 may be formed by the specimen A in which a plurality of the wire coil elements are stranded. Otherwise, the main wire portion 12 may be provided by the specimen B and C in which both end portions of the elongation core 13 is tapered off toward its end, portions (13a, 13b) so as to give them a high flexibility.

The elongation core 13 is such that it shares bending stresses when the guide wire 1 is subjected to a bending deformation. This protects the wire coil elements 3 against the accidental rupture which would otherwise be caused upon inserting the wire-stranded helical hollow tube 2 into and pulling it from the needle tip 6. Since the head plug 14 is secured to both the ends of the elongation core 13, it makes the guide wire 1 insertable in any direction from its rear end and front end portion, while at the same time, rendering it selectively insertable among the rear end and front end portion depending on the diseased condition to be cured. This also makes the guide wire 1 durable enough to be reused several times.

Figure 12:
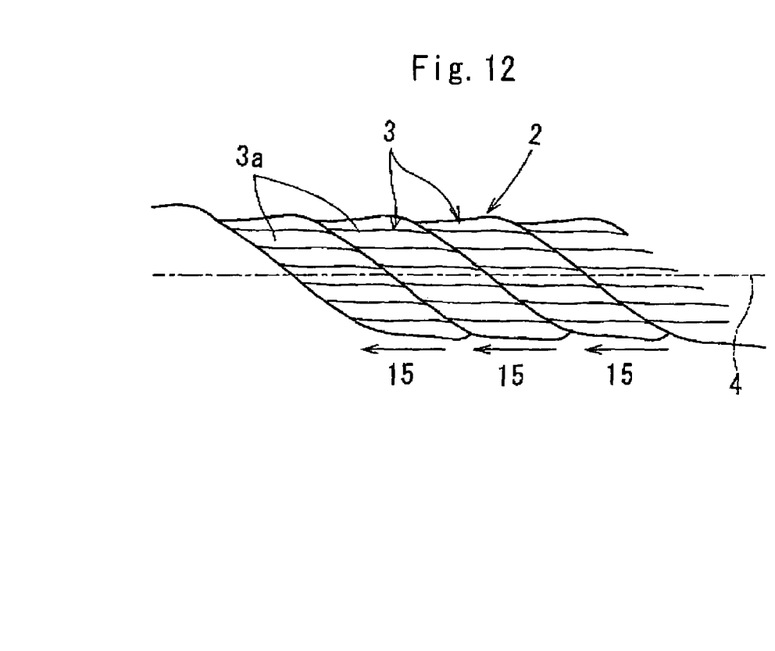
FIG. 12 is a plan view of a medical guide wire partly shown according to a third embodiment of the invention.
Figure 13:
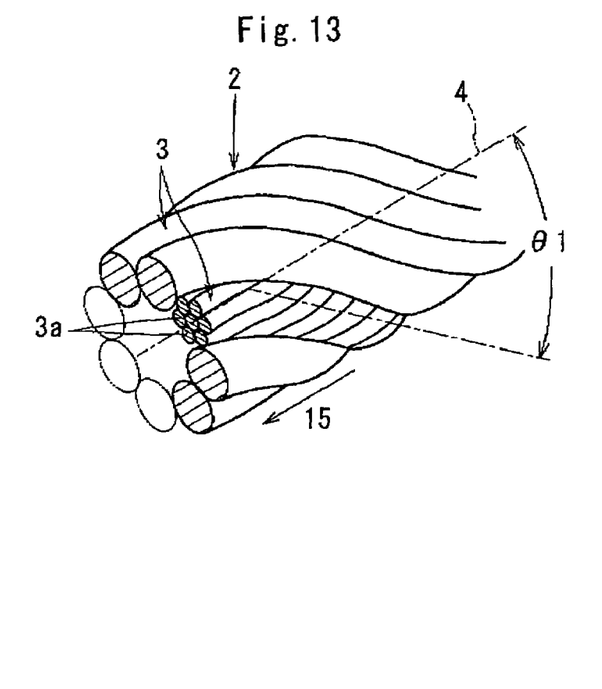
FIG. 13 is a perspective view of the medical guide wire partly shown.

FIGS. 12 and 13 show a third embodiment of the invention in which a stranding direction 15 of line wires 3a of the wire coil elements 3 is the same or substantially the same to an axial direction 4 of the wire-stranded helical hollow tube 2. Namely, the line wires 3a are wound such that the stranding direction 15 is substantially in parallel with the axial direction 4 of the wire-stranded helical hollow tube 2.

This arrangement makes it possible to smoothly slide the wire-stranded helical hollow tube 2 within the puncture needle 5 so as to enable the guide wire 1 to a smooth insertion and pull-out operation against the puncture needle 5.

Upon providing the wire-stranded helical hollow tube 2, eighteen wire coil elements 3 are used to strand them in the Z-direction so as to form a wire coil structure measured 0.81 mm in diameter.

The line wires 3a (0.04 mm in diameter) are used to be twisted in the S-direction so as to form the wire coil elements 3 measured 0.12 mm in diameter (seven line wires stranded around one core line=1×7 structure).

While the line wires 3a is substantially stranded in the axial direction 4 of the wire-stranded helical hollow tube 2, it is possible to make the guide wire 1 slide smoothly against the edge portion 7 of the needel tip 6 as long as an angular difference remains substantially within 6 degrees between the stranding direction 15 and the axial direction 4. The eighteen wire coil elements 3 are not necessarily stranded in the Z-direction and may be twisted in the S-direction, however, it is indispensable to strand the line wires 3a in the direction mutually opposite to the direction which the wire coil elements 3 are twisted.

In the related art guide wire in which the single one wire is helically wound to fort the helical coil tube. When the helical tube slides at the edge portion 7a of the needle tip 6a, the helical tube easily stretches to reveal the clearance between the coil segments which are likely to hitch in the edge portion 7a so as to engage with the edge portion 7a.

On the contrary, according to the invention, the wire-stranded helical hollow lube 2 is such that the wire-stranded helical hollow tube 2 is unlikely to reveal the clearance between the coil segments. In addition, the line wires 3a is stranded substantially in the axial direction 4 of the wire-stranded helical hollow tube 2, i.e., stranded in the lengthwise direction of the puncture needle 5. This structure exerts the wire-stranded helical hollow tube 2 to slide along the puncture needle 5 when the wire-stranded helical hollow tube 2 meets any of the knife edge ends 7A~7D of the edge portion 7 of the needle tip 6. This enables the guide wire 1 to a smooth insertion and easy pull-out operation against the needle tip 6 so as to provide the guide wire 1 with a significantly smooth manipulatability.

MODIFICATION FORMS

It is to be noted that an outer surface of the wire-stranded helical hollow tube 2 may be partly or entirely subjected to a diameter-reducing procedure by means of swaging or die mould work. An outer surface of the wire coil elements 3 may be similarly worked. With the diameter-reducing procedure thus provided, it is possible to impart a smooth surface and an improved rigidity to the wire coil elements 3 so as to insure a good slidability against the puncture needle 5 and a good insertion against the vascular vessel.

The wire-stranded helical hollow tube 2 may be formed by twisting the wire coil elements 3 under the twist-resistant load, and thermally treated to remove the residual stress to insure a good rotation-following capability and straightness. Upon forming the wire-stranded helical hollow tube 2, a part or an entire portion of the wire coil elements may be made of an austenitic stainless steel, shape-memory alloy or super-elastic alloy (e.g., Ni—Ti). Upon forming the wire-stranded helical hollow tube 2, only a part of the wire coil elements 3 may be stranded.

What is claimed is:

1. A medical guide wire formed by a helical hollow wire body which is arranged to retractably move against a needle tip of a puncture needle;
   said helical hollow wire body being formed into a wire-stranded helical hollow tube by stranding a multitude of wire coil elements;
   said wire coil elements of said wire-stranded helical hollow tube having a stranding angle of 55 degrees or less against an axial direction of said wire-stranded helical hollow tube, and further having an angle more than plus 2 degrees upward inclusive or an angle less than minus 2 degrees downward inclusive against a knife edge angle of said needle tip as an angular range;
   said needle tip forming a rake surface sharpened by cutting said puncture needle with two-step angles against an axial direction of said puncture needle, said knife edge angle being one which has a close-sliding relationship with said wire-stranded helical hollow tube; and
   said puncture needle being combined with said helical hollow wire tube.

2. A medical guide wire formed by a helical hollow wire body which is arranged to retractably move against a needle tip of a puncture needle;
   said helical hollow wire body being formed into a wire-stranded helical hollow tube by stranding a multitude of wire coil elements;
   said wire coil elements of said wire-stranded helical hollow tube being formed from stranded wires and having a stranding angle of 55 degrees or less against an axial direction of said wire-stranded helical hollow tube, and further having an angle more than plus 2 degrees upward inclusive or an angle less than minus 2 degrees downward inclusive against a knife edge angle of said needle tip as an angular range;
   said needle tip forming a rake surface sharpened by cutting said puncture needle with two-step angles against an axial direction of said puncture needle, said knife edge angle being one which has a close-sliding relationship with said wire-stranded helical hollow tube; and
   said puncture needle being combined with said helical hollow wire tube.

3. A medical guide wire formed by a helical hollow wire body which is arranged to retractably move from a needle tip of a puncture needle;
   said helical hollow wire body being formed into a wire-stranded helical hollow tube by stranding a multitude of wire coil elements;
   said wire coil elements of said helical hollow wire body being formed from stranded wires;
   said wire coil elements of said helical hollow wire body having a stranding direction mutually opposite to a stranding direction which said wire coil elements of said wire-stranded helical hollow tube has;
   said stranding wires of said wire coil elements having a stranding direction substantially in parallel with an axial direction of said helical hollow wire body; and
   said puncture needle being combined with said helical hollow wire tube.

4. The medical guide wire according to claims 1 or 2, wherein a U-shaped or dog-legged tip is preshaped as a preshaped tip at a distal end of said wire-stranded helical hollow tube.

5. A medical guide wire formed by a helical hollow wire body which is arranged to retractably move from a needle tip of a puncture needle;
   said helical hollow wire body being formed into a wire-stranded helical hollow tube by stranding a multitude of wire coil elements;
   said wire coil elements of said helical hollow wire body being formed from stranded wires;
   said wire coiled elements of said helical hollow wire body having a stranding direction mutually opposite to a stranding direction which said wire coil elements of said wire-stranded helical hollow tube has; and
   said stranding wires of said wire coil elements having a stranding direction substantially in parallel with an axial direction of said helical hollow wire body.

* * * * *